(12) United States Patent
     Lin

(10) Patent No.: US 9,524,579 B2
(45) Date of Patent: *Dec. 20, 2016

(54) ORIENTATING AN OBLIQUE PLANE IN A 3D REPRESENTATION

(71) Applicant: Roger Lin, Shaker Heights, OH (US)

(72) Inventor: Roger Lin, Shaker Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,978

(22) Filed: Nov. 16, 2015

(65) Prior Publication Data

US 2016/0078669 A1    Mar. 17, 2016

Related U.S. Application Data

(63) Continuation-in-part of application No. 13/086,791, filed on Apr. 14, 2011, now Pat. No. 9,189,890.

(60) Provisional application No. 61/342,561, filed on Apr. 15, 2010.

(51) Int. Cl.
```
G06K 9/00      (2006.01)
G06T 15/20     (2011.01)
G06T 7/00      (2006.01)
A61B 5/055     (2006.01)
A61B 6/03      (2006.01)
A61B 8/00      (2006.01)
G06T 19/00     (2011.01)
```
(52) U.S. Cl.
     CPC .............. *G06T 15/20* (2013.01); *A61B 5/055* (2013.01); *A61B 6/032* (2013.01); *A61B 6/037* (2013.01); *A61B 8/00* (2013.01); *G06T 7/004* (2013.01); *G06T 7/0012* (2013.01); *G06T 19/00* (2013.01); *G06T 2200/04* (2013.01); *G06T 2207/30004* (2013.01); *G06T 2219/008* (2013.01)

(58) Field of Classification Search
     CPC ........................ G06T 19/00; G06T 2219/008
     See application file for complete search history.

(56) References Cited

U.S. PATENT DOCUMENTS 4,674,046 A * 6/1987 Ozeki ............... A61B 6/4447
                                                  324/312
7,942,745 B2 * 5/2011 Ikeda ................. A63F 13/06
                                                  340/12.22
8,373,659 B2 * 2/2013 Barney .............. G06F 3/0487
                                                  345/158
(Continued)

OTHER PUBLICATIONS

Sarkar et al ("Intuitive Interface for the Exploration of Volumetric Datasets", 2008).*

*Primary Examiner* — Avinash Yentrapati
(74) *Attorney, Agent, or Firm* — Brian Asquith

(57) ABSTRACT

Systems and methods are provided to facilitate orientation of a plane with respect to a three-dimensional representation. A device is presented utilizing at least one of an accelerometer, gyroscope, or combination thereof, enabling determination of a current position and/or orientation of the device. Outputs from the accelerometer, gyroscope, etc., are captured and orientation of a plane displayed with regard to the three-dimensional representation is accordingly adjusted to correspond with the position of the device. Imaging information relating to the three-dimensional representation and the plane can be captured facilitating analysis of the respective slice of the three-dimensional representation associated with the plane.

20 Claims, 9 Drawing Sheets

(56) References Cited

U.S. PATENT DOCUMENTS

| | | | |
|---|---|---|---|
| 2005/0018902 A1* | 1/2005 | Liang | G06T 7/0081 |
| | | | 382/154 |
| 2005/0024323 A1* | 2/2005 | Salazar-Ferrer | G06F 3/0213 |
| | | | 345/156 |
| 2005/0261567 A1* | 11/2005 | Harder | A61B 5/055 |
| | | | 600/407 |
| 2008/0154952 A1* | 6/2008 | Waldinger | G06T 19/00 |
| 2008/0309618 A1* | 12/2008 | Okada | A63F 13/04 |
| | | | 345/157 |
| 2009/0060309 A1* | 3/2009 | Tsujii | G06T 15/08 |
| | | | 382/131 |
| 2009/0252682 A1* | 10/2009 | Hillman | A61B 5/0059 |
| | | | 424/9.1 |
| 2010/0130855 A1* | 5/2010 | Lundberg | A61B 8/00 |
| | | | 600/437 |
| 2010/0225582 A1* | 9/2010 | Ohta | A63F 13/02 |
| | | | 345/158 |
| 2010/0225583 A1* | 9/2010 | Ohta | A63F 13/02 |
| | | | 345/158 |
| 2011/0028825 A1* | 2/2011 | Douglas | G06F 19/321 |
| | | | 600/407 |
| 2011/0260968 A1* | 10/2011 | Ye | G06F 3/0346 |
| | | | 345/158 |
| 2013/0004048 A1* | 1/2013 | Tsujii | G06T 15/08 |
| | | | 382/131 |
| 2014/0195016 A1* | 7/2014 | Yamamoto | G06F 3/017 |
| | | | 700/83 |

* cited by examiner

ORIENTATING AN OBLIQUE PLANE IN A 3D REPRESENTATION

RELATED APPLICATIONS

This application is a continuation-in-part of U.S. patent application Ser. No. 13/086,791, filed on Apr. 14, 2011, and entitled "ORIENTATING AN OBLIQUE PLANE IN A 3D REPRESENTATION. Further, this application claims the benefit of U.S. Provisional Application Ser. No. 61/342,561, filed on Apr. 15, 2010, entitled "Computer Peripheral". The entirety of the above-captioned applications are incorporated herein by reference.

TECHNICAL FIELD

The subject specification relates generally to digital imaging and in particular to the selection and manipulation of images.

BACKGROUND

A wealth of data is available facilitating the creation of digital representations having a seeming 3-Dimensional (3D) solidity. For example, in the field of medical imaging, digital data is captured from imaging systems such as magnetic resonance imaging (MRI), computed tomography (CT), ultrasound, and the like, enabling a solid image representation to be rendered on a display device. During analysis of the data, a radiologist can, by means of a mouse, trackball, or other system, advance a plane through the digital representation, and at a desired point, a current plane or slice, can be reviewed. Hence, a radiologist, surgeon, or other medical personnel can review images slices and compare the images with expected or anticipated results, unexpected results, etc., to facilitate detection of injury, e.g., broken limb, or an abnormality such as cancerous growth.

Typically a slice is moved through a 3D image (e.g. created from a data set) by employing an orthogonal coordinate system, where any point in a plane is uniquely represented by three orthogonal coordinates signing distances in relation to three mutually perpendicular axes, e.g., x, y, and z. In a conventional system, a plane is orientated in a 3D representation by selecting the position of the plane in any of three orthogonal 2D representations, e.g., a first representation along the x axis, a second representation along the y axis, and a third representation along the z axis. Moving a plane in any of the three orthogonal representations results in a corresponding motion of the plane in the 3D representation. However, owing to employing any of the orthogonal 2D representations to facilitate selection and movement of a plane, for any given operation of selection/movement, the orientation of the plane is only effected in two dimensions in the 3D representation. Hence, orientation of a plane, particularly an oblique plane, can be awkward and time consuming.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of this summary is to present some concepts related to some exemplary non-limiting embodiments in a simplified form as a prelude to the more detailed description of the various embodiments that follow.

Systems and methods are provided which include generation and display of a plane with respect to a 3D representation and capture of information associated with the plane. In various, non-limiting embodiments, combinations of accelerometer(s) and gyroscope(s) can be utilized to determine an orientation of a device, wherein, based on position and orientation determinations performed with regard to positioning signals, and associated vectors, generated by the accelerometer(s) and/or gyroscope(s) the plane in the 3D representation can be correspondingly orientated. In a non-limiting embodiment the accelerometer(s) and gyroscope(s) can be located in a first device (e.g., a planar orientation device, (POD)) communicatively coupled to a second device, where the first device can be orientated as desired with the orientation being determined on the second device, and a plane correspondingly presented on a display device associated with the second device.

In another, non-limiting embodiment, during initialization, a plane can be initialized at any desired position, e.g., located at a mid point in the 3D representation image and orientated at 90°, or located at an end of the 3D representation, or any other user definable position/orientation. Further, during initialization, the respective position of the POD can be synchronized with the respective orientation of the plane.

In another, non-limiting embodiment interactive controls can be employed to facilitate performing such functionality as print, zoom, capture data, affect image quality and display, etc. In a further, non-limiting embodiment, any of capturing position data, generating position data, or calculating position of a plane can be halted, temporarily or permanently, to facilitate repositioning of the POD without affecting a current orientation of an oblique plane.

In another, non-limiting embodiment image data can be captured in a sequential manner facilitating subsequent playback of the planar control process as part of a subsequent operation such as diagnosis. In a further, non-limiting embodiment, image data can be captured and stored either locally or on a remote system, where such image data can include the 3D representation, oblique plane and pertaining information (e.g., plane angles in x, y, and z), imaging information (e.g., an image slice) generated in association with the oblique plane.

In a further embodiment, the POD can have attached thereto an instrument (e.g., a probe), and a position and/or alignment of the instrument can be determined based upon one or more signals generated by the POD.

These, and other embodiments, are described in more detail below.

DETAILED DESCRIPTION

Overview of Planar Orientation

As discussed in the background, analysis of data represented in a digital 3D rendering can be facilitated by moving a plane through the rendering, where the plane is moved and described in relation to coordinate axes and planes typically referred to as x, y, and z. In medical parlance, the three planes are termed axial plane (or transverse plane), coronal plane, and sagittal plane.

However, manipulation and orientation of a plane which can be angled through, and angled in relation to, any of the x, y, z, axial, coronal, and/or sagittal planes would be beneficial. Such an angled plane is referred to herein as an oblique plane. Unfortunately, manipulation of an oblique plane by employing such devices as a mouse, trackball, digital pen/pad, etc., can be an awkward and a time consuming process, particularly when employing an approach of utilizing three orthogonal 2D representations to orientate a plane in a 3D representation as described earlier. For example, when employing a mouse to generate an oblique slice, an operator may in one approach, have to draw a slice on a display (e.g., two dimensional screen) by clicking or selecting respective pixels identifying the "corners" of the slice and then select new pixels to indicate a location of the new plane.

Effectively, the plane and conventional selection device(s) (e.g. a mouse or trackball) do not have direct spatial relationships with each other, in that the selection device must first identify a plane of interest (e.g., select plane to be moved) and then move the plane, where the operation of selecting and moving a plane comprises a plurality of steps or operations. Hence, a mouse is being utilized in a 2D manner, a 2D plane is selected, and then the movement in 3D is presented on a display (as described in the Background). It would be preferable if the device controlling the oblique slice could operate in a 3D manner, e.g., in free-space, and the oblique slice was manipulated/orientated in parallel, in realtime, corresponding to direct spatial movements of the device. The term free-space is used herein to convey the concept of a device being moved, orientated, rotated, or any combination thereof, in any three-dimensional space, and the three-dimensional environment in which the device is moved, etc.

The various embodiments presented herein relate to at least one of a medical imaging, magnetic resonance imaging, nuclear magnetic resonance imaging, magnetic resonance tomography, radiography, scintigraphy, 3D tomography, positron emission tomography, ultrasonography, computed tomography, etc.

Figure 1:
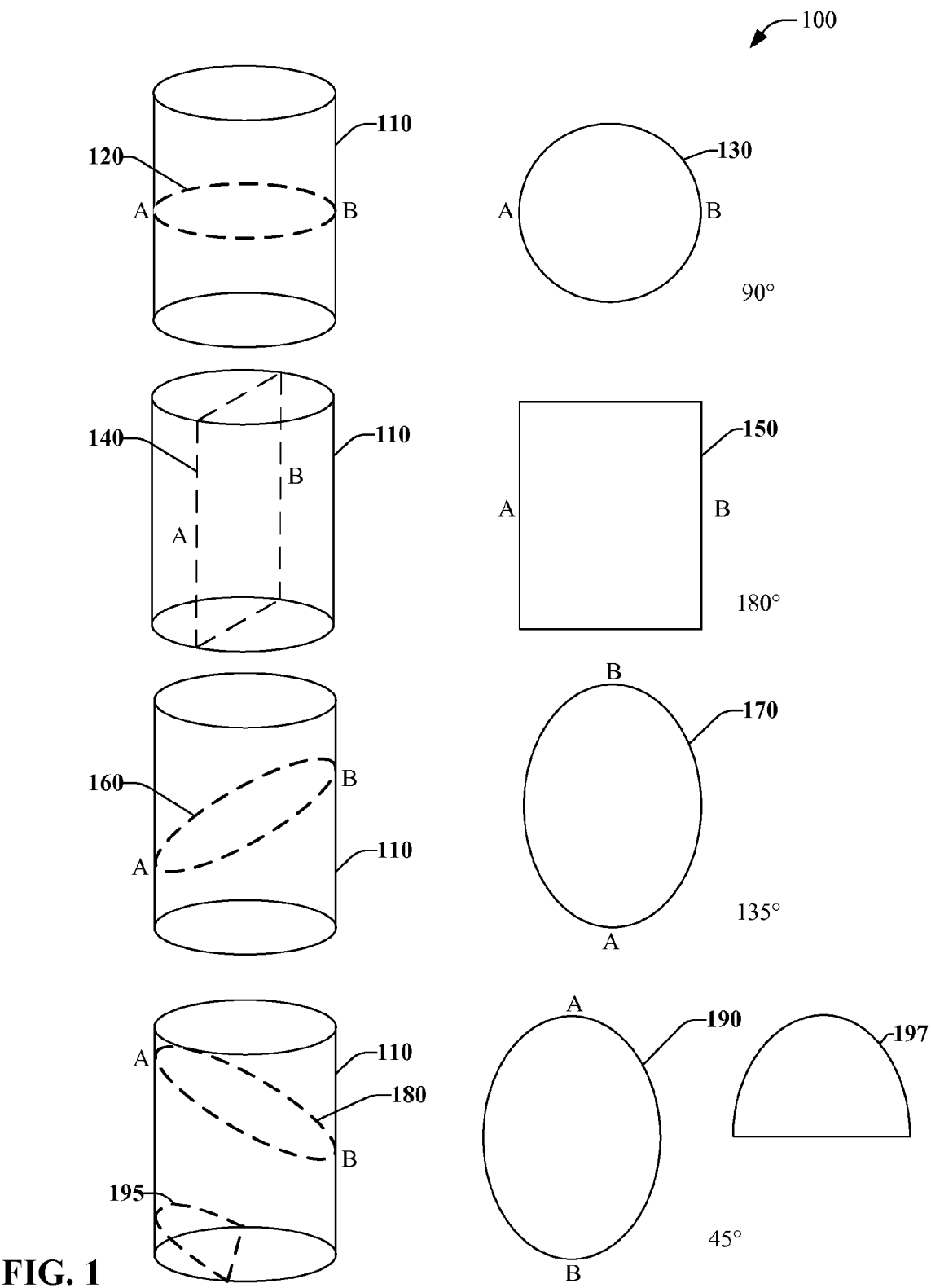
FIG. 1 is a block diagram illustrating an exemplary, non-limiting embodiment of manipulating a slice within a 3D representation.

FIG. 1, illustrates an exemplary, non-limiting embodiment of manipulating a slice within a 3D representation. Rendering 110 is a 3D representation of an object, where the 3D representation comprises data generated by any of a plurality of sources, e.g., medical imaging system, engineering visualization system, architectural design system, and the like, as discussed above. Rendered in the 3D representation are respective planes 120, 140, 160, 180, and 195, wherein each plane is orientated at a different angle. For example, plane 120 is angled at 90°, plane 140 is angled at 180°, plane 160 is angled at 135°, and plane 180 is angled at 45°. Shown on the right hand side of FIG. 1, are image slices 130, 150, 170, and 190, corresponding to respective planes 120, 140, 160 and 180, presenting the different regions swept through the 3D representation by respective slices 120, 140, 160 and 180, and, accordingly, the different amounts of information presented within a plane for a particular orientation. As shown, as the plane is moved through a plurality of orientations, the imaging slice captured by the plane changes. For example, the area of image slice 130 is a fraction of the area of image slice's 150 or 170. Further, as shown in FIG. 1, vertical position of the plane can be altered, plane 160 is located approximate to the midpoint of rendering 110, while plane 180 has been shifted vertically with respect to the midpoint of rendering 110. Further, a plane does not have to be entirely contained within rendering 110, for example, plane 195 is only partially located within rendering 110 and results in a partial image slice 197 in comparison with image slice 190 generated by plane 180.

It is to be appreciated that, while a 3D rendering of a medical application is presented herein, the various exemplary, non-limiting embodiments presented herein can be applied to any applications involving digital rendering and representation of objects where a slice can be advanced through the rendering. Such applications, in a non-limiting, non-exhaustive list can include digital animation, a digital game system, a design (e.g., a 3D digital representation of a vehicle), architectural design, and the like. Effectively, any system where a 3D solid is represented by an array of pixels, wireframe, finite element analysis data, animation data, nodes, edges, polygonal modeling, polygonal mesh, Non-uniform rational basis spline (NURBS), splines and patches, primitives modeling, sculpt modeling, voxels, and the like.

Planar Orientation and Image Manipulation

Figure 2:
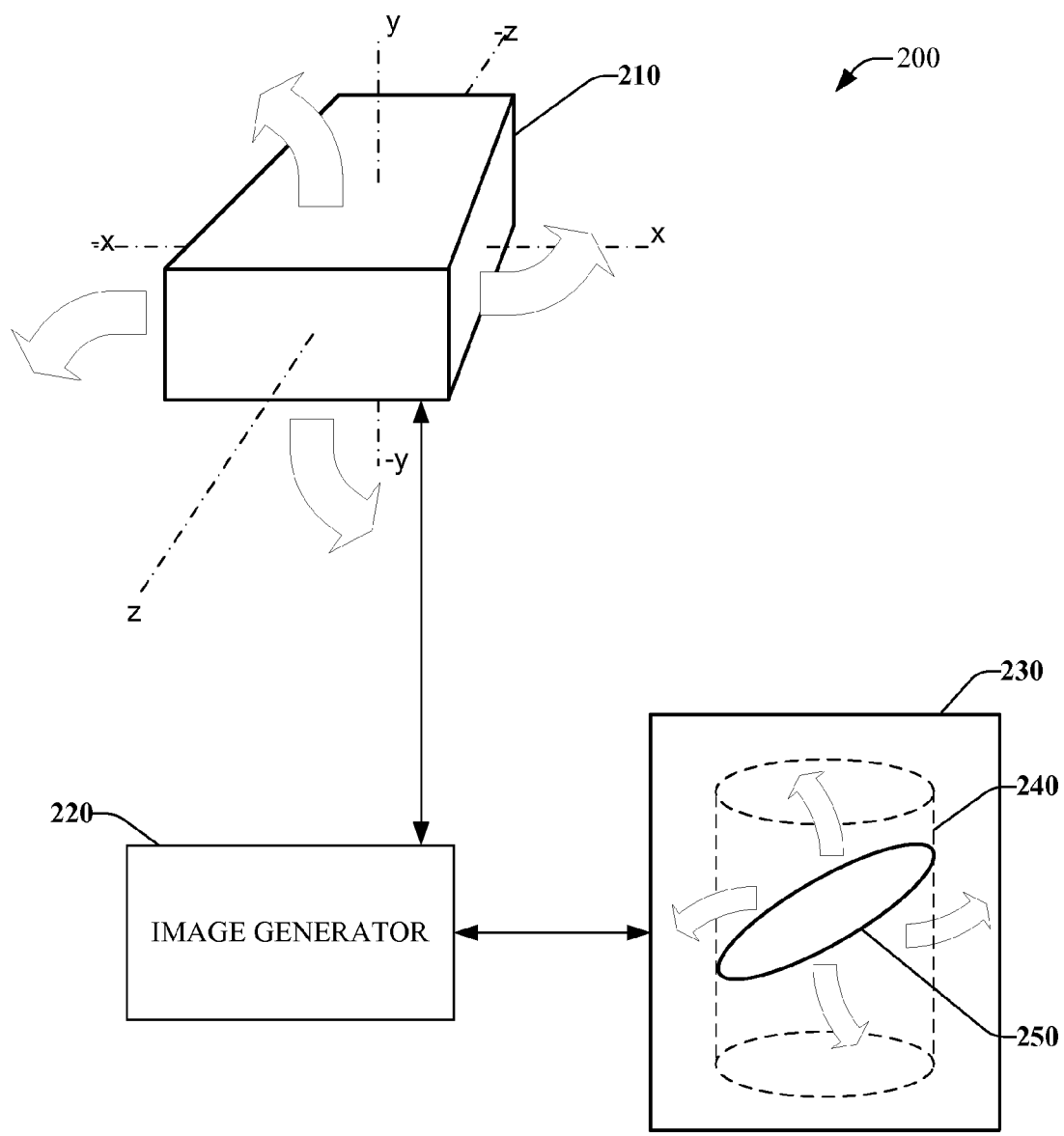
FIG. 2 is a block diagram illustrating an exemplary, non-limiting embodiment for effecting orientation of a plane in association with a 3D representation.

As discussed above, adjusting the orientation of a plane within a 3D representation can be an awkward and time consuming operation, where such orientation is typically achieved by a user employing a computer mouse in a 2D environment (e.g., on a mouse pad) while adjusting a plane with three 2D representations to achieve movement of the plane in a 3D environment (e.g., in conjunction with a 3D representation on a 2D display). With respect to one or more non-limiting aspects of plane manipulation as described above, FIG. 2 shows a block diagram illustrating an exemplary, non-limiting embodiment for effecting orientation of a plane in association with a 3D representation. A device 210 for manipulating a plane with 3D movement is communicatively coupled to image generator 220. Image generator 220, in accordance with positioning signals received from device 210 facilitates manipulation of a plane 250 which can be displayed in association with a 3D representation 240 on a display device 230. For the sake of readability, device 210 is referenced herein as a planar orientation device, POD 210. As illustrated in FIG. 2, as the orientation of POD 210 is adjusted in free-space, plane 250 is correspondingly adjusted with regard to the orientation of POD 210, as shown by the respective orientating arrows. It is to be appreciated that while not fully conveyed in FIG. 2, as well as being tilted by any angle with respect to the x, y, or z axes, POD 210 can also be moved orthogonally with respect to any of the x, y, or z axes, e.g., POD 210 can be moved vertically with respect to the y axis, resulting in plane 250 being moved vertically in the 3D representation, effecting the change in location of plane 180 vs. plane 160 (see FIG. 1) with respect to the midpoint of the 3D representation 110. It is to be further appreciated that for the various embodiments as described herein, the orientation of plane 250 does not have to equate to the orientation of POD 210, as shown in FIG. 2, POD 210 is aligned in a position approximately normal to each of axes x, y, and z, and their respective negative axes, while plane 250 is aligned at approximately 135°. Setting of the respective tilting ratio(s) and angle(s) and/or displacement distance(s) and ratio(s) can be altered by any suitable means such as keypad entry (keyboard not shown) or a slider presented on display 230, where the slider can be positioned to effect 1:1 ratio, 1:3 ratio, 5:1 ratio, etc.

Unlike employing a mouse (2D movement) to orientate an image plane, by utilizing a positioning device, e.g., POD 210, in free-space, the motion of plane 250 corresponds to the motion of POD 210. For example, POD 210 can be tilted to a 30° orientation and also physically lowered, which effects plane 250 to also be represented with a 30° degree orientation as well as moving vertically, (e.g., being lowered) through the 3D representation 240.

It is to be appreciated that the degree of movement of a plane (e.g., plane 250) with respect to a 3D representation (e.g., 3D representation 240) can be a function of the data employed to create the 3D representation. For example, the various components comprising system 200 can be configured such that a degree of tilt of POD 210 will result in a corresponding degree of tilt of plane 250, e.g., POD 210 is tilt 1° then plane 250 is tilt 1°, POD 210 is tilt 5° then plane 250 is tilt 5°, POD 210 is tilt 87° then plane 250 is tilt 87°, etc. However, tilt of POD 210 can also be configured to be a ratio of the effected tilt of plane 250. For example, for each 1° of tilt of POD 210, plane 250 is tilt 5°, hence the ratio is 1:5. It is to be appreciated that any tilt ratio can be utilized, e.g., 1:3, 5:1, 10:1, etc. The concept of ratio of movement of the POD 210 and corresponding movement of plane 250 also pertains to rotation of POD 210 and plane 250, where rotation can be determined by gyroscope, vector integration, and the like, as described infra.

Further, the distance with which a plane 250 moves vertically (e.g., up and down in the y,–y directions), horizontally (e.g., sideways in the x, –x, z, –z directions), or combination thereof, e.g., diagonally, can be configured such that an amount of displacement of POD 210 in free-space generates an equivalent amount of displacement of plane 250 in 3D representation 240. For example, if POD 210 is moved vertically upward 5 mm, plane 250 is also moved vertically upward 5 mm in 3D representation 240. However, the relative displacement of POD 210 and plane 250 can be configured to be a respective portion, e.g., displacement of POD 210 is set to be a ratio of 3:1 with respect to plane 250, and for every 3 mm motion of POD 210, plane 250 moves 1 mm. Relative displacement of POD 210 and plane 250 can be further affected by the viewing area provided by display 230, e.g., where display 230 is of such a size that 3D representation 240 can be presented thereon with a magnification of 10× the lifesize object from which 3D representation 240 is generated, moving POD 210 1 mm can result in moving plane 10 mm on display 230, however, owing to the 10× magnification, the "real" movement of plane 250 is 1 mm. Relative displacement of POD 210 and plane 250 can also further be affected by the amount of data available from which 3D representation 240 is rendered, e.g., a 1 mm displacement of POD 210 may equate to moving between one plane of pixels comprising 3D representation 240 and the next pixel plane.

Figure 3:
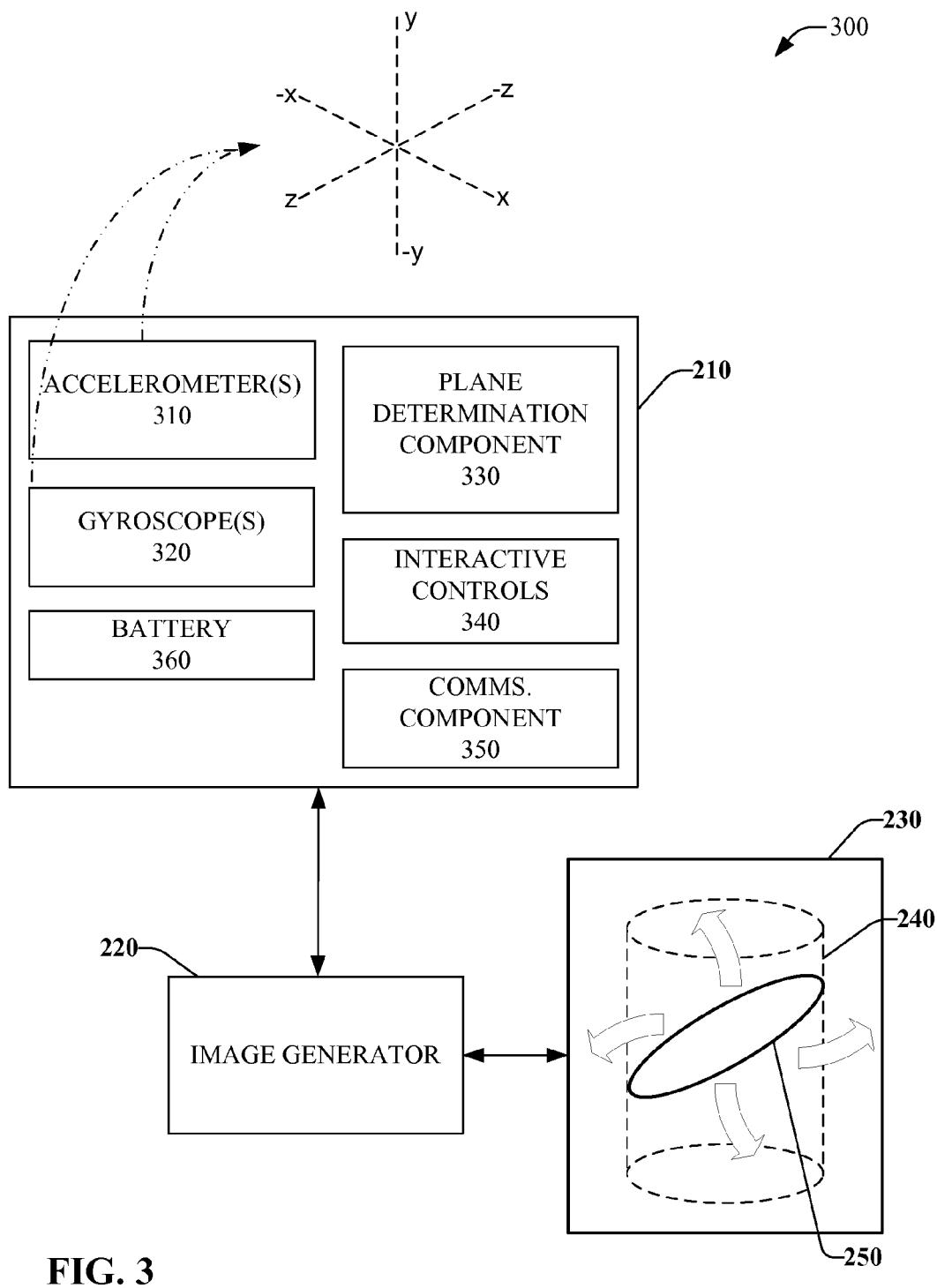
FIG. 3 is a block diagram illustrating an exemplary, non-limiting embodiment to facilitate orientation of a plane in a 3D representation.

Turning to FIG. 3, is a block diagram illustrating an exemplary, non-limiting embodiment to facilitate orientation of a plane in a 3D representation. POD 210 is communicatively coupled to an image generator 220, wherein, as the orientation of POD 210 is adjusted in free-space, plane 250 is correspondingly adjusted in the 3D representation 240 presented on display device 230.

One or more accelerometer(s) 310 (e.g., a multi-axis accelerometer) and gyroscope(s) 320 can be utilized, either singly or in combination, to facilitate determination of the orientation and movement of POD 210. In an exemplary, non-limiting embodiment, three accelerometers 310 can be utilized to measure linear and angular accelerations orthogonally with respect to each other, e.g., in the orthogonal directions x, y, and z, and their respective negative direction counterparts. Each of the three accelerometers 310 can measure the x, y, and z gravity components and generate respective signals which are received at plane determination component 330. Based upon the signals received from the three accelerometers 310, plane determination component 330 can generate one or more gravity vectors, or positioning vectors, e.g., a vector for each of the x, y, and z axes, from which the current orientation of POD 210 can be determined and accordingly, plane 250 orientated with respect thereto.

In an exemplary, non-limiting embodiment, accelerometers 310 can comprise of microelectromechanical systems (MEMS) located on an integrated circuit or chip. Accelerometers 310 MEMS can comprise of one or more small cantilevered beams, where motion of POD 210 can effect deflection of the one or more cantilevered beams, and based upon the deflection, the degree of acceleration in any given direction can be determined. In an exemplary, non-limiting embodiment accelerometers 310 can be utilized to determine orientation of POD 210 with respect to gravity. Where three accelerometers 310 are employed, one accelerometer for each respective x, y, and z axis, a gravity component in each of the x, y, and z directions can be determined. It is to be appreciated that while accelerometers 310 have been described herein based upon a cantilevered beam operation, any suitable means for determining acceleration, and accordingly, orientation of a device can be employed with the various embodiments presented herein. For example, in a non-exhaustive listing, accelerometer(s) 310 can operate with respect to a field, e.g., voltage in an electrical field, current within an electrical field, measurement of magnetic field strength in a magnetic field, etc.

Gyroscope 320 can be utilized to determine rotation of POD 210, as opposed to measuring the tilt of POD 210, which as described above can be a functionality performed by accelerometers 310. Hence, if a viewer of the 3D representation is initially viewing the image from a frontal perspective, e.g., a 3D representation of a person's face, by utilizing gyroscope 320 rotation of POD 210, e.g., laterally about the y axis, can be determined enabling a view from the rear of the head to now be prominently displayed on display 230.

Many operations and settings (e.g., white balance, brightness, etc.) regarding the presentation of the 3D representation 240 and the plane 250 can be controlled/adjusted at the display 230 itself. Alternatively, one or more image controls can be located on POD 210. In an exemplary, non-limiting embodiment, POD 210 can comprise of one or more interactive controls 340, where such interactive controls 340 can comprise of any means suitable to facilitate execution and control of a desired operation such as "print image", "print image slice", "capture image", "capture image slice", "change imaging contrast", "change brightness of image", and the like. Accordingly, such means can comprise of touch pad(s), button(s), slider(s), etc.

In an exemplary, non-limiting embodiment, interactive controls 340 can be utilized to temporarily disable generation of positioning signals from POD 210. For example, a user, in the process of orientating a plane 250 with POD 210, may have POD 210 positioned in an uncomfortable or awkward position and wants to re-locate POD 210 in a position that is more comfortable. If the POD 210 is simply moved to the comfortable position then the orientation of plane 250 will be undesirably moved. However, to prevent the plane 250 being correspondingly moved, a button, or the like, in the interactive controls 340 can be pressed, initiating a temporary cessation of signals being generated and transmitted from POD 210. Hence, as POD 210 is re-orientated to a more favorable position, plane 250 remains with the orientation at the time of signal cessation. Once POD 210 is re-orientated to the new position, the interactive control 340, e.g., a button, can be re-pressed and the orientation of plane 250 can be recommenced is accordance with orientation of POD 210 from the new position. In an exemplary, non-limiting embodiment, at the moment the interactive control 340 is re-selected, e.g., re-pressed, signals from the respective accelerometers 310 can be recalibrated, or synchronized, with regard to the new position and the new calibration, or new synchronization, can act as the reference point in regard to subsequent orientation and movement of plane 250.

In a further, exemplary, non-limiting embodiment, interactive controls 340 can comprise of one or more touch sensors. During operation of POD 210 a user locates a finger on a touch sensor and as POD 210 is orientated and moved, plane 250 also moves. However, if it is desired to temporarily or permanently cease operation of POD 210 (and accordingly, signal generation and plane analysis by image generator 220), the user can remove their finger from the touch sensor, whereupon the finger can be replaced at a subsequent time facilitating subsequent operation of POD 210.

In an exemplary, non-limiting embodiment, power can be supplied to the various components comprising POD 210 by a battery 360, or other suitable means for power generation and/or supply located at POD 210. In an alternative embodiment, POD 210 can be powered using other conventional means such as a mains power supply (and power transformer if required), secondary power from a device associated with POD 210, e.g., image generator 220, and the like.

Further, any suitable means for communication between POD 210 and image generator 220 can be employed and, in a non-exhaustive listing, can comprise of communications over a hard-wired network, wireless-network, combination thereof, and any other suitable communication infrastructure to facilitate transport of signals, data, commands, and the like, between POD 210 and image generator 220. Further, wireless signals can be radio waves, infrared, optical, etc. Communication component 350 (and correspondingly communications component 440, see FIG. 4) can be employed to facilitate communication between POD 210 and image generator 220, where communication components 350 and 440 can be utilized to format data with the necessary communications protocol, encapsulate data, and the like, as required to facilitate communications.

Figure 4:
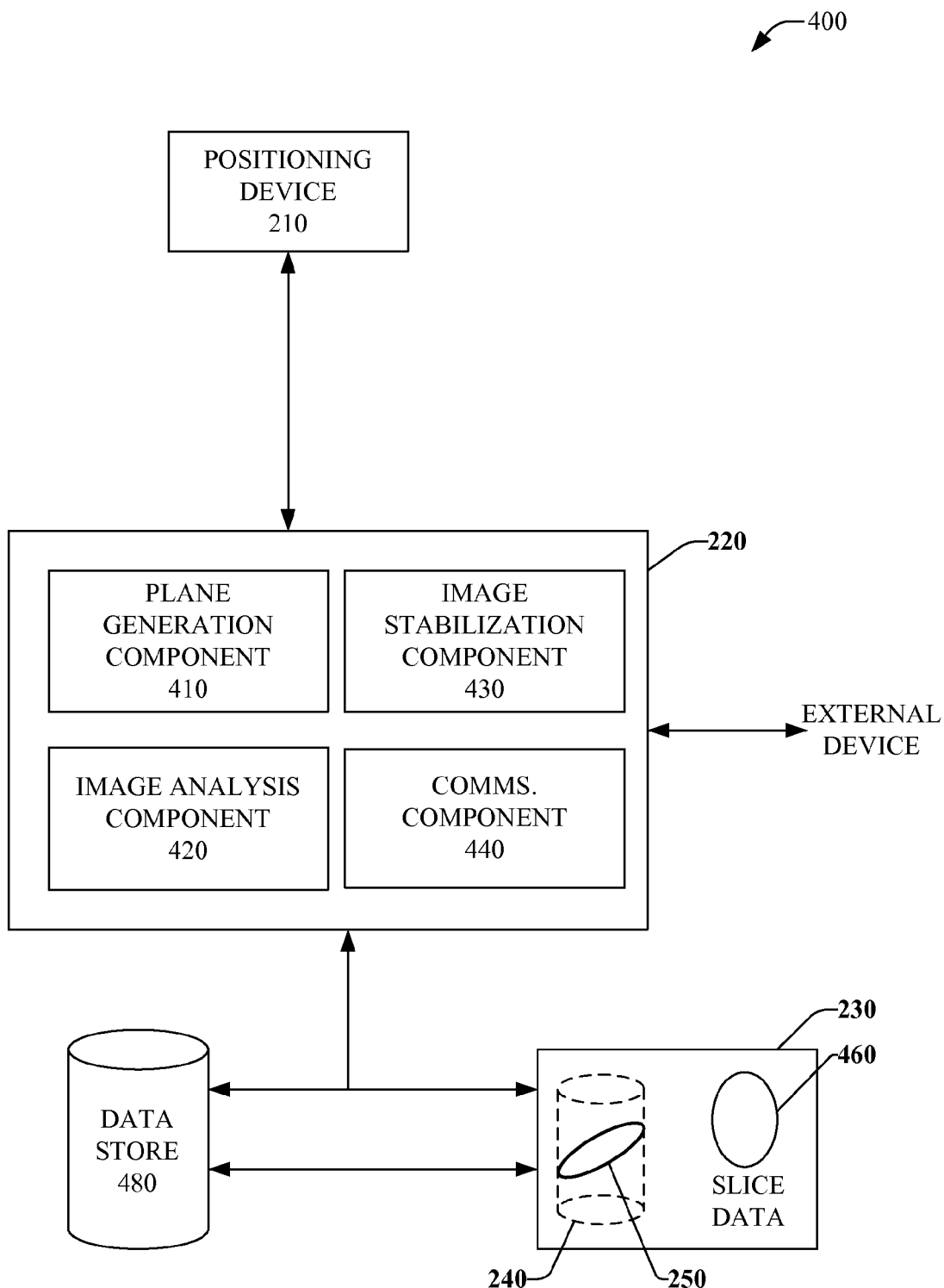
FIG. 4, is a block diagram illustrating an exemplary, non-limiting embodiment to facilitate determination and orientation of a plane in a 3D representation.

FIG. 4, is a block diagram illustrating an exemplary, non-limiting embodiment to facilitate determination and orientation of a plane in a 3D representation. POD 210 is communicatively coupled to an image generator 220, wherein, as the orientation of POD 210 is adjusted in free-space, plane 250 is correspondingly adjusted in the 3D rendering 240 presented on display device 230 communicatively coupled to image generator 220.

Image generator 220 comprises a plane generation component 410 which receives positioning signals (e.g., positioning vectors) from POD 210, and based thereon, determines the position of POD 210 and accordingly, the orientation of plane 250 in the 3D representation presented on display 230. Signals are received from POD 210 via communications component 4440 in a manner as described with regard to communications component 350.

One or more positioning signals, as generated by accelerometer(s) 310, and gyroscope 320, or combination thereof, are received at plane generation component 410, whereupon plane generation component 410 employs the signals to determine the position of the POD 210. Further, while employing signals generated by accelerometer(s) 310 to determine tilt of POD 210 and accordingly plane 250, in an exemplary, non-limiting embodiment, it is possible to perform an integration function on the acceleration signal(s) provided by accelerometer(s) 310 to facilitate calculation of the absolute change of POD 210 spatial position with regard to free space. Hence, plane determination component 330 can be employed to determine a spatial translation of POD 210 as well as the orientation of POD 210. Further, plane determination component 330 can further employ angular acceleration signals and rotational orientation signals to calculate absolute rotational position of POD 210. For example, POD 210 is tilted 10°, rotated 7° and also lowered by 5 centimeters, such motion of the device in free-space can be determined by processing of the respective motion signals received from the accelerometer(s) 310 and/or gyroscope(s) 320.

During initialization, e.g., start up of any or all of POD 210, image generator 210, and/or display 230, an initial plane can be positioned at a predetermined position. For example, plane 250 can be located at a "neutral" position with respect to a 3D representation, e.g., at a central position having a 90° orientation such as plane 120 with respect to 3D representation 110, as shown in FIG. 1. Alternatively, the initial position can be located at the bottom or top of a 3D representation, e.g., a plane located at either end of 3D representation 110. In another alternative embodiment, the initial plane can be located at a predefined position such as a location of a bone break in a 3D representation of a broken leg, or the site of a tumor in a 3D representation pertaining to a cancerous growth. Furthermore, the initial plane can be located at a position as preferred by an operator of display 230, e.g., a radiographer prefers that the initial plane always be located one third vertically into the image with an orientation of 60°.

Further, during initialization, while the initial plane is being generated, the position of POD 210 is also determined at the time of initialization, such that if POD 210 is not in an initial "stable" condition, e.g., POD 210 is laying on a flat surface, then the position and orientation of POD 210 at the time of initialization is coordinated with the initial orientation of plane 250. For example, a user of POD 210 always starts with the POD 210 held and orientated with an approximate 20° tilt, while plane 250 is initialized at a neutral position with respect to the 3D representation, e.g., plane 250 is initialized at a position comparable to plane 120 with respect to 3D representation 110, as shown in FIG. 1. Hence, during initialization, the positioning signals received from accelerometer(s) 310 and/or gyroscope 320 where the POD 210 is orientated to 20° are equated, e.g., synchronized, to a plane 250 having an orientation of 90°, e.g., plane 120 of FIG. 1. Once initialization has been performed, POD 210 can be re-orientated with a corresponding re-orientation of plane 250. Hence, with regard to the example, following initialization, if POD 210 is tilted from an angle of 20° to 30°, i.e., a 10° displacement, plane 250 which was initially orientated at 90° will undergo a corresponding 10° change in displacement, resulting in plane 250 now being shown with an orientation of 100° (i.e., 90°+10°).

It is to be appreciated that the above angles of orientation, as with any angles presented herein, are provided to aid understanding of the various embodiments described herein, and POD 210 can be oriented at angle, orientation, position, degree of rotation, etc., in any of axes x, −x, y, −y, z, −z, axial plane, transverse plane, coronal plane, sagittal plane, and the like, where orientation of POD 210 can occur while supported on a flat surface, e.g., a table, as well as when in free-space, e.g., being held in free-space.

As shown in FIG. 4, image generator 220 is communicatively coupled to display 230. Display 230 can present 3D representation 240, plane 250, and also any information pertaining to plane 250 and/or 3D representation 240, for example slice data 460 comprising an image slice and respective information, such as time of generation of image slice, orientation of image slice, and the like.

Any suitable techniques and methods can be employed to facilitate rendering and presentation of any of 3D representation 240, plane 250, image slice 460, and the like. For example, the 3D representation 240 can be shown with a lower brightness or contrast than plane 250, such that as plane 250 moves through representation 240, imaging data relating to the pixels, data points, etc., relating to the slice currently being swept by plane 250 is shown in higher contrast, resolution, coloration, and the like, enabling imaging features to be readily discerned.

Further, at any moment during orientation of POD 210 and rendering of plane 250 with respect to 3D representation 240, the image data can be captured, and if necessary stored in a storage device, such as data store 480 which can be communicatively coupled to any, or all, of POD 210, image generator 220 and/or display 230. Such capturing of image data enables an operator of system 200 to capture image data which can be subsequently analyzed, etc. For example, a radiologist may be employing one or more embodiments as presented herein as part of an analysis of a tumor. To facilitate determination of the position and/or size of the tumor, a plane 250 can be placed on a left periphery of the tumor and the image data captured, e.g., respective position of plane 250 with regard to 3D representation 240. The plane 250 can subsequently be moved to a right periphery of the tumor and image data captured at this position, e.g., respective new position. With the two pieces of image data a determination can be made regarding the size of the tumor between the right periphery and left periphery, and by repeating the process of capturing image data from plane(s) 250 respectively placed with regard to the tumor, further determinations can be made regarding the size of the tumor in multiple directions, as well as the volume of the tumor, for example. As mentioned above, any given plane 250 can be captured (e.g., by activation of an interactive control 340) during operation of POD 210 and stored in data store 480.

For example, any of the plane(s) 250 and their associated image data 460 employed in determining the size of the tumor can be saved to data store 480, along with any plane 250 and image data 460 orientated through the tumor.

It is to be appreciated that while POD 210, image generator 220 and display device 230, and data store 480 have been illustrated as separate devices, the various embodiments presented herein, are not so limited. For example, image generator 220, display 230, and data store 480 can be combined into a single, self-contained device, creating a device having the ability to receive signals from POD 210, display 3D representation(s) 240, plane(s) 250, and any associated data and images 460. In another exemplary, non-limiting embodiment, POD 210, image generator 220 and display device 230 can be combined into the same device, facilitating plane orientation on the same device as which the plane (e.g., plane 250) is rendered with respect to a 3D representation 240. For example, a single device can comprise of accelerometer(s) 310, a gyroscope 320, or any other means suitable to facilitate determination of the orientation and movement of the single device. A 3D representation 240 can be presented on the device, and as the device is re-orientated a plane 250 can be rendered in the 3D representation. In an exemplary, non-limiting embodiment, the 3D representation can remain statically displayed on the display 230 of the single device while the plane 250 is kept at a constant planar orientation with respect to the display 230 viewing surface (e.g., 90°). In an alternative, exemplary, non-limiting embodiment, the plane 250 is kept static while the 3D representation is re-orientated as the orientation of the single device is adjusted. In a non-exhaustive listing, the single device can be any device comprising necessary accelerometer(s) and gyroscope(s) and a means for display, such as an IPHONE, IPAD, smart phone, PC tablet, and the like.

Further, image generator 220 can further comprise an image stabilizer component 430, which can be employed to facilitate stabilization of plane 250 in 3D representation 240, along with presenting a stable image slice 460. For example, an operator holding POD 210 may not be able to hold POD 210 sufficiently still in free-space, e.g., operators hand shakes. Image stabilization techniques can be employed to generate a stable plane 250, and accordingly a stable image slice 460. For example, the operators hand shaking may cause the POD 210 to tilt through a range of ±4°, image stabilization can be employed to reduce the effects of the shake, e.g., determine a median position, and a steady position for plane 250 is available. Image stabilization can be turned ON/OFF, e.g., by employing interactive controls 340. Further, image stabilizer 430 can be executed to determine the degree of image stabilization required for an operator and the degree of stabilization can be stored for future use by the operator using POD 210.

It is to be appreciated that application of the systems and methods presented herein are myriad, and as discussed earlier, can be applied to many fields utilizing 3D representation of real and/or imaginary objects, where such fields include engineering design and analysis, architectural design and analysis, animation, graphic design, graphical rendering, and the like. One particular application, as mentioned, is in the field of medical imaging. The various aspects and embodiments presented herein can enable a radiologist to expeditiously move between various planes (e.g., plane 250) of a volume image (e.g., 3D representation 240), thereby enabling a radiologist to readily discern and quantify characterizations pertaining to anatomical structures, such as bowel loops, vessels and lymph nodes, etc. Application of such systems and methods, as presented herein, can enable a radiologist to expeditiously identify, in the case of a bowel obstruction, a transition point owing to the ability of POD 210 to follow the contours and orientation of the bowel lumen. With regard to lymph nodes, employing POD 210 can facilitate in improved measurement of true long and short axes which can be difficult when performed with respect to the traditional methods employing axial, coronal and sagittal slices. Further, with regard to tumor analysis and investigation, pathologic characterizations can be more accurately performed owing to the radiologist employing POD 210 to better visualize borders relating to the tumor from a plurality of angles.

It is to be further appreciated that while the foregoing pertains to moving POD 210 to a particular orientation, and as desired or required, capturing image data, e.g., image slice 460, at the particular orientation of POD 210, capturing of image data can be a continual operation. For example, image data, e.g., movement of plane 250 in 3D representation 240 and/or image data 460 can be continually captured and stored sequentially enabling a "movie" to be generated depicting motion of the POD 210, and corresponding motion of plane 250 and image data (e.g., image slice and coordinates) 260 for viewing at a subsequent time. For example, a radiologist can record a sequence of motion of a plane along a 3D representation of a bowel. At a subsequent time, a physician can review the image sequence as part of a diagnosis procedure.

Further, where a 3D representation has been colorized, contrast imaged, or other means to distinguish imaging regions, motion of a plane can be based upon moving from one location of a colored pixel to a subsequent colored pixel. For example, for a plurality of abnormal growths in a 3D representation of a lung pixels have been identified and colored yellow, while normal lung growth is represented with pixels colored green. An initial location of plane 250 can be at the first pixel, or pixel cluster, having yellow coloration. Upon performing any required analysis of the pixel/pixel cluster, plane 250 can be advanced to the next pixel/pixel cluster having yellow coloration. Advancement of plane 250 between pixel/pixel clusters can be effected by any suitable means, such as a "next" button in the interface controls 340, or as facilitated by a keyboard (e.g., pressing a tab key, pressing a space bar, etc.), mouse, or the like, associated with system 200, e.g., communicatively coupled to POD 210, image generator 220, and/or display 230.

It is to be further appreciated, that while POD 210 has primarily been described previously as a hand held device, the components comprising POD 210 can be combine into any device or arrangement facilitating orientation of plane 250. For example a suitable device can be a glove, wherein the glove is worn and as the hand is respectively tilted, moved, orientated, and the like, plane determination component 330, interactive controls 340, accelerometer(s) 310, gyroscope(s) 320, and/or combination thereof, can result in an according movement of plane 250 in 3D representation 240.

Figure 5:
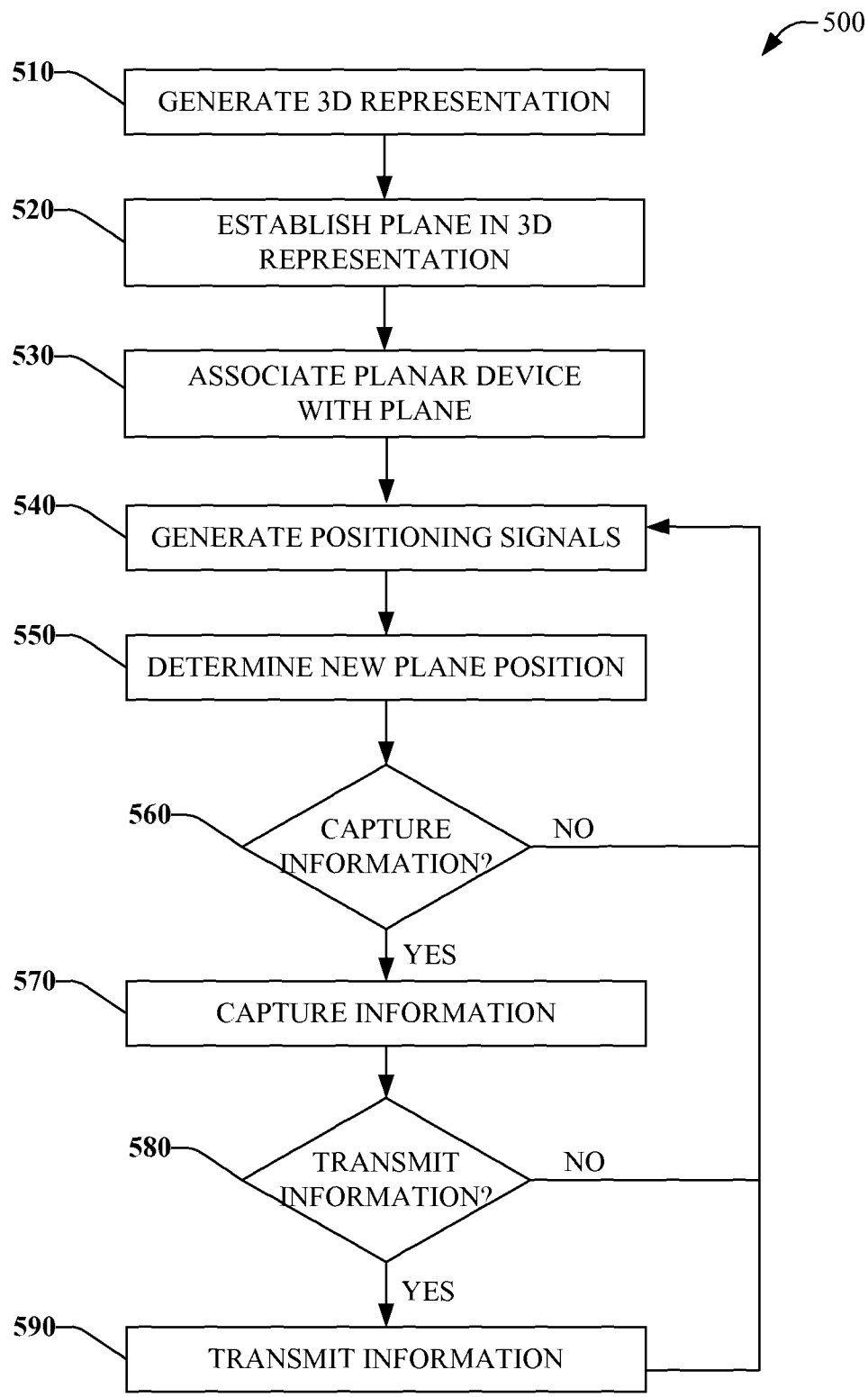
FIG. 5 depicts a flow diagram illustrating an exemplary, non-limiting embodiment for orientating a plane within a 3D representation and capturing information associated with the plane.

FIG. 5 depicts a flow diagram illustrating an exemplary, non-limiting embodiment for orientating a plane within a 3D representation and capturing information associated with the plane. The embodiment of FIG. 5 can be utilized by the POD 210, image generator 220 and display 230 system as shown in FIGS. 2-4.

At 510, a 3D representation is generated. The 3D representation can be generated based upon imaging data received from any of a plurality of sources, e.g., medical imaging system, engineering visualization system, architectural design system, and the like.

At 520 a plane is established in the 3D representation. As illustrated in FIG. 1, a plane can be positioned in any desired location, e.g., in a non-exhaustive listing, any of a midpoint, top, bottom, tilted, location of interest (e.g., tumor on a 3D representation of a lung), or any other operator defined position.

At 530 a planar orientating device (POD) to facilitate orientation and movement of the plane is associated with the plane. The POD comprises components which generate signals in response to any of an orientation, a rotation, a positional movement, or combination thereof, where such components comprise any of accelerometer(s), gyroscope(s) and the like.

At 540 orientation of the POD is adjusted and positioning signals are generated by components comprising the POD in accord with the orientation of the POD. For example, accelerometers can be employed to determine the angle of tilt of the POD along with the position of the POD vertically, horizontally, diagonally, etc. Further, rotation of the POD can be determined based upon signals generated by a gyroscope, or by signals generated by the accelerometer(s).

At 550 the respective positioning signals generated by and received from any of the accelerometers or gyroscopes can be employed to facilitate determination of the orientation of the POD. For example, three accelerometers can be employed to generate orientation vectors with respect to any of axes x, −x, y, −y, z, −z, etc., and based thereon a positioning vector can be determined, from which the plane can be correspondingly orientated. For example, if the POD is tilted 0.5° the accelerometers generate signals indicating the effects of the 0.5° orientation on each of the accelerometers, and an overall positioning vector can be calculated, such that there is a corresponding tilt in the plane of 0.5°.

At 560 a determination can be made as to whether information associated with the new plane orientation is of interest and is to be captured. If the determination is no, the flow returns to 540 for generation of the next positioning signal(s).

At 570, in response to the determination that information associated with the new plane orientation is of interest, the information can be captured. For example, the plane in the 3D representation is orientated such that imaging information associated with the plane is to be captured, e.g., pixel data from an image slice pertaining to the plane in the 3D representation is captured along with positioning information of the plane. It is to be appreciated that the requirement to capture information can be a continual operation as a plane sweeps through a plurality of angles of motion. Data can be captured based on any defined parameter such as time or angle. Captured image slices for the plane can be sequentially tagged and stored sequentially. At a later time, the sequence of image slices can be replayed presenting a "movie" of the plane through the 3D representation and associated image data.

At 580 a further determination can be made regarding whether to transmit any information, either captured, or stored. In the event that the information is not to be transmitted, the flow returns to 540 for the next generation of positioning signals.

In the event that the information is be transmitted, any of the 3D representation, plane, image slice, positioning data, and the like can be transmitted to an external device for remote viewing and/or storage.

Figure 6:
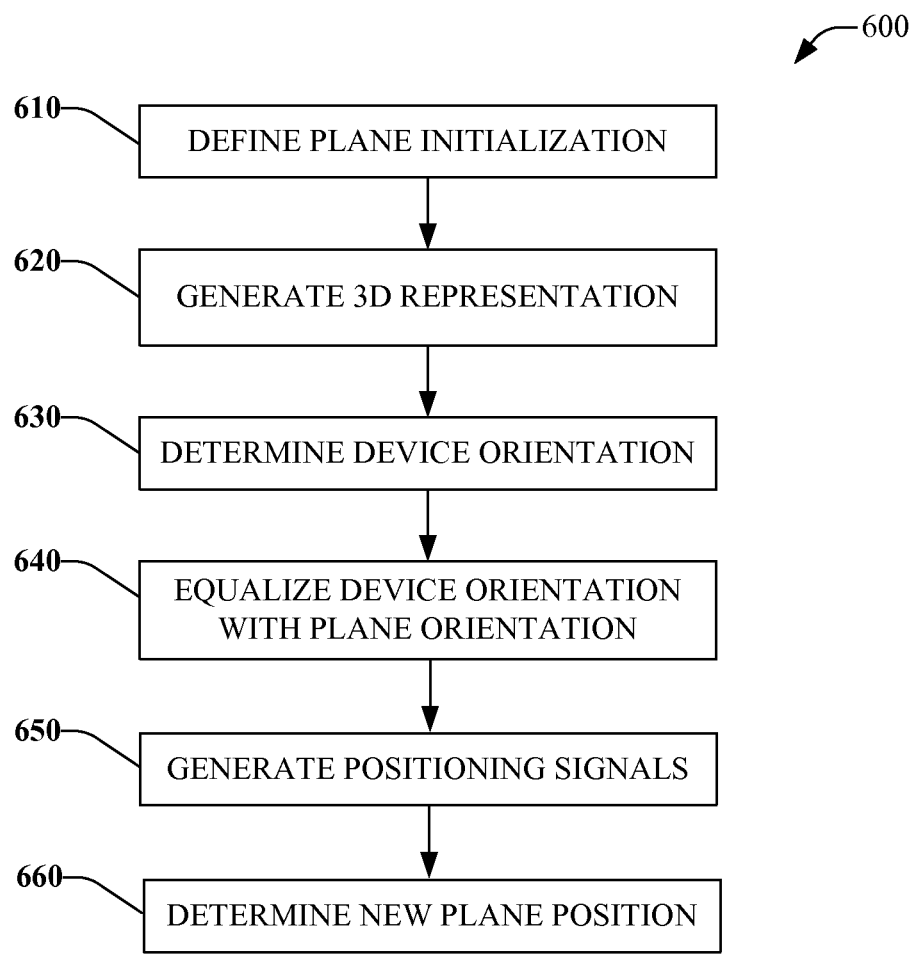
FIG. 6 depicts a flow diagram illustrating an exemplary, non-limiting embodiment for initializing a plane within a 3D representation and a planar orientation device.

FIG. 6 depicts a flow diagram illustrating an exemplary, non-limiting embodiment for initializing a plane within a 3D representation and a planar orientation device (POD). The embodiment of FIG. 6 can be utilized by the POD 210, image generator 220 and display 230 system as shown in FIGS. 2-4.

At 610, an orientation with which a plane is to be displayed within a 3D representation is defined. During initialization, e.g., start up of any or all of POD 210, image generator 210, and/or display 230, an initial plane can be positioned at a predetermined position. For example, a plane can be located at a "neutral" position with respect to a 3D representation, e.g., at a central position having a 90° orientation such as plane 120 with respect to 3D representation 110, as shown in FIG. 1. Alternatively, the initial position can be located at the bottom or top of a 3D representation, e.g., a plane located at either end of 3D representation 110. In another alternative embodiment, the initial plane can be located at a predefined position such as a location of a bone break in a 3D representation of a broken leg, or the site of a tumor in a 3D representation pertaining to a cancerous growth. Furthermore, the initial plane can be located at a position as preferred by an operator of display 230, e.g., a radiographer prefers that the initial plane always be located one quarter vertically into the image with an orientation of 70°.

At 620, a 3D representation is generated with a plane rendered therein, wherein the plane is rendered at the defined position and orientation.

At 630, the orientation of the POD is determined. For example, the POD may be located in an at-rest position sitting flat on a desk. Alternatively, the POD may be located in a position in free-space and the orientation of the POD is to be determined. Signals generated by accelerometer(s) and/or gyroscope(s) associated with the POD are captured and the orientation of the POD is established. For example, signals generated by and received from the accelerometers indicate that the POD is orientated with a 5° tilt with respect to the x axis.

At 640, the position and orientation of the initial plane is coordinated (or calibrated) with the determined orientation of the POD. For example, if the plane is angled at 90° (e.g., horizontal plane 120, shown in FIG. 1) and the POD is determined to be orientated with a 5° tilt, the signals being received from the accelerometers can be equalized to take into account the 5° tilt and, accordingly, the orientation of the POD is considered to be 90°.

At 650, the POD is re-orientated, new positioning signals are received and a new position vector is determined for the POD. For example, the POD is tilted to a 10° tilt, and according position signals are generated, i.e., 10°-5°=5°.

At 660, the new position vector is employed to apply a corresponding degree of tilt to the plane in the 3D representation, whereupon the plane is re-orientated in accord with the new position vector.

Figure 7:
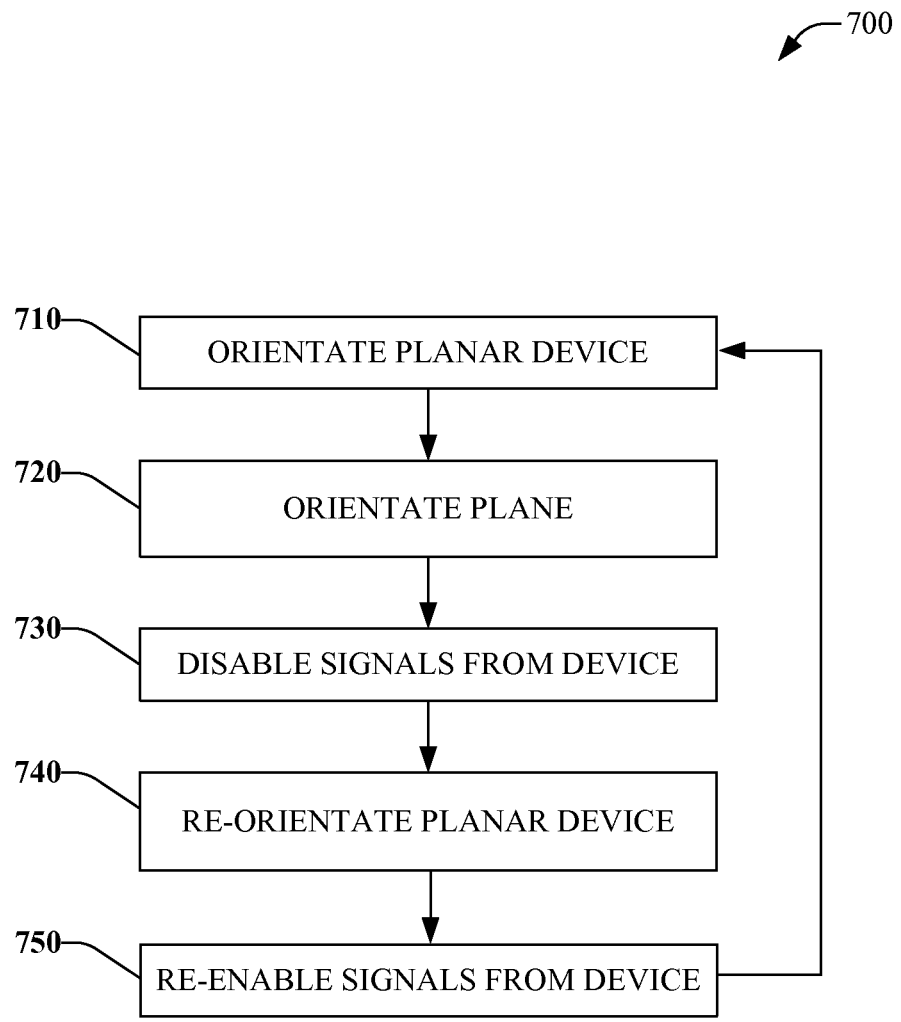
FIG. 7 depicts a flow diagram illustrating an exemplary, non-limiting embodiment for orientating a planar orientation device without orientating a plane.

FIG. 7 depicts a flow diagram illustrating an exemplary, non-limiting embodiment for orientating a planar orientation device (POD) without orientating a plane. The embodiment of FIG. 7 can be utilized by the POD 210, image generator 220 and display 230 system as shown in FIGS. 2-4.

At 710, a POD is being employed to orientate a plane, wherein the POD is being orientated to facilitate a corresponding orientation of the plane.

At 720, the plane is being orientated in a 3D representation with regard to positioning signals received from the POD. However, a case may arise where while the plane is being orientated, the POD is being held in an uncomfortable position, for example.

At 730, signals being generated from the POD can be disabled, enabling the POD to be re-orientated, e.g., to a more comfortable position. However, rather than the plane being orientated in conjunction with the movement of the POD, by disabling signals from the POD, the POD can be moved freely while the plane is held in a last position before the signals were disabled. It is to be appreciated that while the above describes disabling signals from the POD, any means for disabling movement of the plane can be utilized. For example, positioning signals are generated at the POD but calculation of the positioning vector(s) is disabled at the POD, or at the image generator. Signals can be disabled by activating a button or similar at the POD, on the image generator, or at the display device.

At 740, with the orientation of the plane being disabled, the POD is re-orientated to a new position.

At 750, once the POD is located/orientated in the new position, (e.g., a more comfortable position), coordination of signals between the orientation of the POD and the orientation of the plane is re-enabled, wherein as the POD is further orientated the plane is correspondingly orientated.

Assemblies for Image Directed Therapy

Figure 8:
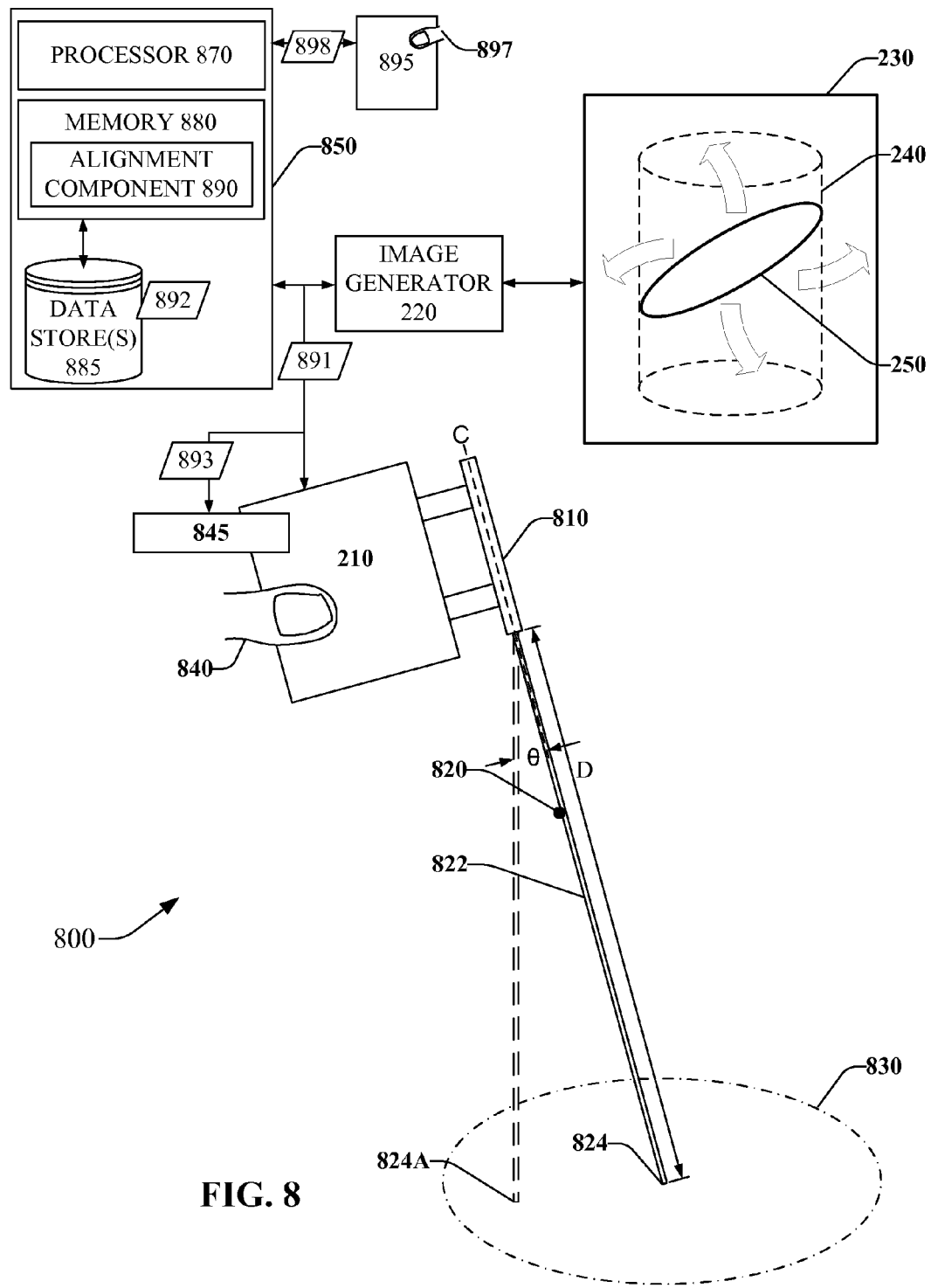
FIG. 8 is a block diagram illustrating an exemplary, non-limiting embodiment of controlling position and/or orientation of an instrument within a 3D representation.

FIG. 8 illustrates a system 800, wherein a POD 210 is utilized for image directed therapy. As shown in FIG. 8, the POD 210 is attached to an instrument holder 810 which is utilized to attach (couple) an instrument 820 to the POD 210. In another embodiment, the instrument 820 can be attached directly to the POD 210. The instrument 820 can be any suitable diagnostic or therapeutic instrument, including but not limited to, a needle for injection, a needle for aspiration, a biopsy needle, a probe utilized for ablation, a surgical instrument, etc. The instrument 820 can comprise of any required parts, e.g., with the example presented in FIG. 8 being a needle, a probe, etc., the example instrument 820 has a shaft 822 and a tip 824. A location of the tip 824 relative to the POD 210 and/or the instrument holder 810 can be determined (known) based upon determining a distance D between the tip 824 and a point on the POD 210 and/or the instrument holder 810. The location of the tip 824 can be further defined based upon an angle θ and/or an offset between the centerline C of the instrument holder 810 and a location of the tip 824, or 824A when the instrument 820 has a bent or offset alignment.

By attaching the POD 210 to the instrument 820, it is possible to direct (align) the instrument 820 with a reference to a site of interest, e.g., a body region 830, with guidance of the instrument 820 being provided by POD 210. In an embodiment, the POD 210 can be connected to a display (e.g., display 230), wherein an image (e.g., 3D representation 240) can be generated (e.g., by the image generator 220) and presented on the display, wherein the image can be utilized to assist an operator in achieving desired placement of the instrument 820.

In an embodiment, the operator can be an entity 840 (e.g., a human), wherein the entity 840 can view the image on the display and based upon the presented plane 250, the entity 840 can adjust alignment of the POD 210, and accordingly, the attached instrument 820, relative to the body region 830.

In another embodiment, the operator can be a robot 845 (e.g., an electro-mechanical device or machine), wherein the robot 845 can be communicatively coupled to a positioning module 850. The positioning module 850 can comprise of a processor 870 and a memory 880, wherein the memory 880 comprises data that is accessible to the processor 870 and instructions that can be executed by the processor 870. A data store(s) 885 can be utilized to store data utilized by one or more components included in the positioning module 850. With more particularity, the positioning module 850 can include an alignment component 890, wherein the alignment component 890 is configured to receive at least one positional output 891 from the POD 210. The alignment component 890 is further configured to process the positional output 891 relative to a desired position 892, wherein the desired position 892 can be a position, a location, an alignment, a depth, a height, a movement, etc., of the shaft 822, the tip 824, etc., of the instrument 820. The alignment component 890 is further configured to compare the positional output 891 with the desired position 892, and based thereon, can generate a positional instruction(s) 893 for a new location of the robot 845 (e.g., a robot grip) to compensate for any difference between the desired position 892 and a current position defined in the positional output 891. The process of positional output 891, position correction, and generation of a new positional instruction 893 and associated correction of the robot 845, and accordingly the position of the instrument 820 can be repeated as necessary during the medical operation. The robot 845 can be controlled by the entity 840, wherein the entity 840 is remotely located from the robot 845 and can communicate with the robot 845 by a controller device (e.g., a joystick) as is known in the art.

In a further embodiment, an entity 897 (e.g., a human) can be altering a position, orientation, etc., of a first POD 895 at a remote location, wherein the first POD 895 is communicatively coupled to the positioning module 850. A positioning signal 898 can be generated by the POD 895 and transmitted to the positioning module 850. The positioning signal 898 can be processed at the positioning module 850 (e.g., by the processor 870 and/or the alignment component 890) and based thereon, the positional instruction(s) 893 can be generated and utilized to control the robot 845 and accordingly, the second POD 210. The entity 897 can view the position of the POD 210 on the display 230 and make positional adjustments based thereon, as previously described.

Operation of the POD 210 by either an entity 840 (or entity 897) or the robot 845 in conjunction with the display 230, the 3D representation 240, the presented plane 250 or the positioning module 850 (and components and data related thereto) can enable determination of a position of the instrument 820 (e.g., the shaft 822 and/or the tip 824) within the body, which can accordingly prevent harm to a patient by assisting the operator to avoid vital structures in the patient's body. In an embodiment, positioning of the POD 210 and, accordingly, the instrument 820, can be calibrated by positioning the POD 210 and/or the instrument 820 at a known location and orientation in relation to the body region 830.

In another embodiment, the POD 210 can contain additional sensors, such as optical, radio, or magnetic sensors, which will allow it to help determine its position in relation to an object, such as a laser, optical, infrared, radio, or magnetic field reference.

Exemplary Computing Device

As mentioned, advantageously, the techniques described herein can be applied to any system supporting the control operations described herein. It can be understood, therefore, that handheld, portable and other computing devices and computing objects of all kinds are contemplated for use in connection with the various embodiments, e.g., effecting orientation of a plane in association with a 3D representation. Accordingly, the below general purpose remote computer described below in FIG. 8 is but one example of a computing device, where the computing device can comprise any of the POD 210, image generator 220, display 230, or external device, as presented above.

Embodiments can partly be implemented via an operating system, for use by a developer of services for a device or object, and/or included within application software that operates to perform one or more functional aspects of the various embodiments described herein. Software may be described in the general context of computer-executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is considered limiting.

Figure 9:
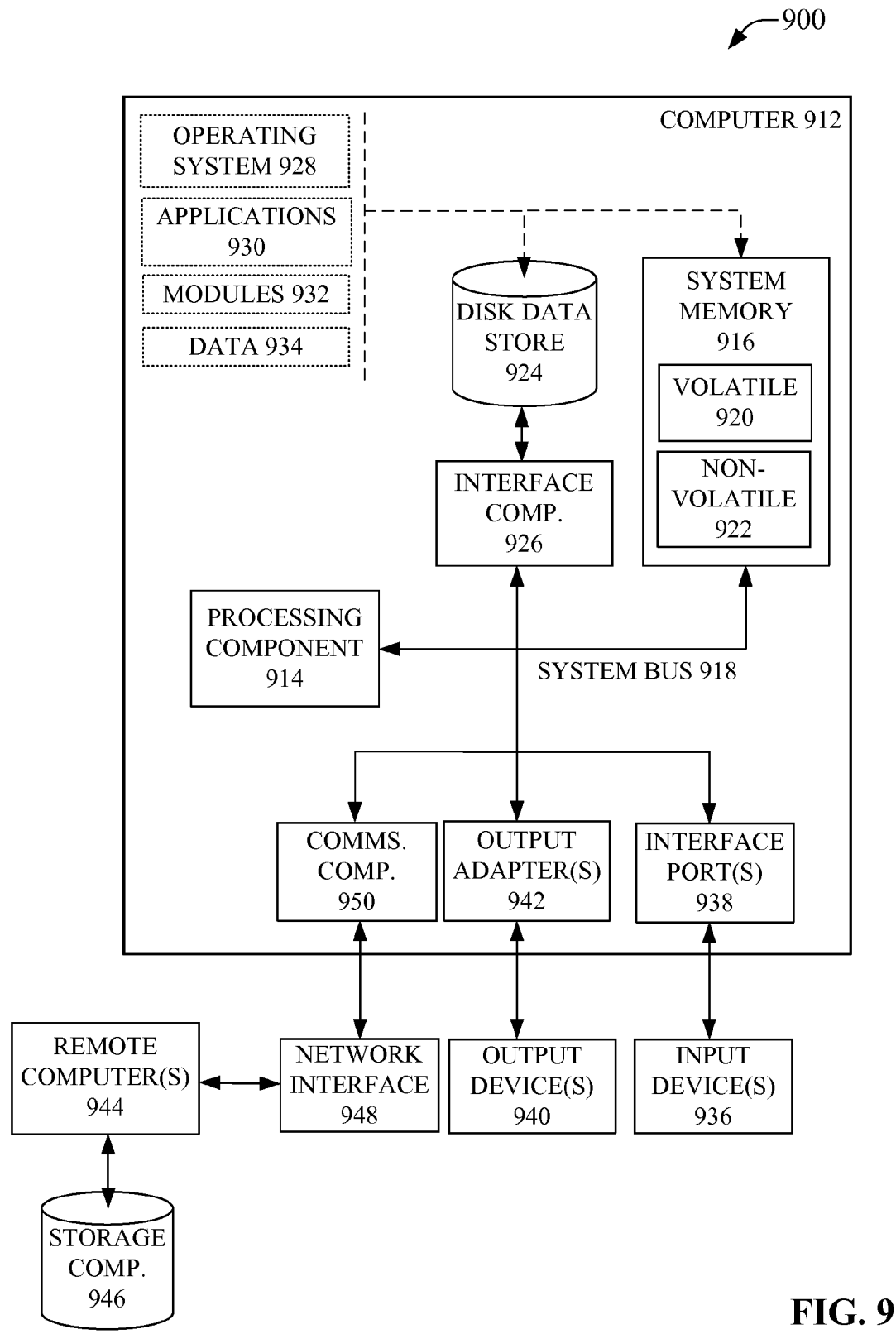
FIG. 9 illustrates an exemplary, non-limiting computing environment facilitating operation of one or more exemplary, non-limiting embodiments disclosed herein.

FIG. 9 thus illustrates an example of a suitable computing system environment 900 in which one or aspects of the embodiments described herein can be implemented, although as made clear above, the computing system environment 900 is only one example of a suitable computing environment and is not intended to suggest any limitation as to scope of use or functionality. In addition, the computing system environment 900 is not intended to be interpreted as having any dependency relating to any one or combination of components illustrated in the exemplary computing system environment 900.

With reference to FIG. 9, an example environment 900 for implementing various aspects of the aforementioned subject matter, including determining an orientation of a device and effecting a corresponding orientation of an associated oblique plane or slice, includes a computer 912. The computer 912 can include any of a processing component 914, a system memory 916, and a system bus 918. System bus 918 is employed to couple system components comprising environment 900, including, but not limited to, the system memory 916 to the processing component 914. The processing component 914 can be any of various available processors, including dual microprocessors and other multiprocessor architectures.

System memory 916 can include volatile memory 920 and non-volatile memory 922. In exemplary, non-limiting embodiments, non-volatile memory 922 can comprise any of read only memory (ROM), programmable ROM (PROM), electrically programmable ROM (EPROM), electrically erasable PROM (EEPROM), or flash memory. In an exemplary, non-limiting embodiment, volatile memory 920 includes random access memory (RAM), which acts as external cache memory, wherein, a non-exhaustive listing, RAM can comprise of synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The basic input/output system (BIOS), containing the basic routines to transfer information between elements within the computer 912, such as during start-up, is stored in non-volatile memory 922.

System bus 918 can be any of several types of bus structure(s) including the memory bus or memory controller, a peripheral bus or external bus, and/or a local bus using any variety of available bus architectures and, in a non-exhaustive listing can include any of 8-bit bus, VESA Local Bus (VLB), Universal Serial Bus (USB), Extended ISA (EISA), Industrial Standard Architecture (ISA), Micro-Channel Architecture (MSA), Advanced Graphics Port (AGP), Intelligent Drive Electronics (IDE), Peripheral Component Interconnect (PCI), Small Computer Systems Interface (SCSI), and Personal Computer Memory Card International Association bus (PCMCIA).

Computer 912 can also comprise removable/non-removable, volatile/non-volatile computer storage media, such as, for example, a disk data store 924. Disk data store 924 can include, in a non-exhaustive listing, any of a magnetic disk drive, floppy disk drive, tape drive, Jaz drive, Zip drive, LS-100 drive, flash memory card, memory stick, or other device providing comparable functionality. Further, disk data store 924 can also comprise storage media separately or in combination with other storage media including, in a non-exhaustive listing, an optical disk drive such as a compact disk ROM device (CD-ROM), CD recordable drive (CD-R Drive), CD rewritable drive (CD-RW Drive) or a digital versatile disk ROM drive (DVD-ROM). A removable or non-removable interface, e.g., interface 926, can be employed to facilitate connection of any of one or more disk data store(s) 924 to the system bus 918.

FIG. 9 further presents software which can act as an intermediary between an operator(s) of components comprising environment 900 and the various components comprising computer system environment 912. In a non-exhaustive listing, software can comprise any of an operating system 928, system applications 930, program modules 932, and program data 934 (e.g., data employed to generate 3D representation(s) 110 and 240). Operating system 928, which can be stored on disk storage 924, facilitates control and allocation of resources of the computer system 912. System applications 930 operate in accord with the management of system resources by operating system 928 through program modules 932 and program data 934 stored either in system memory 916 or on disk storage 924. It is to be appreciated that the subject invention can be implemented with a variety of, or combination of, operating systems.

Input device(s) 936, can be employed by an entity to facilitate entry of commands or information into the computer 912. In a non-exhaustive listing, input devices 936 can comprise a pointing device such as a mouse, trackball, stylus, touch pad, keyboard, microphone, joystick, game pad, satellite dish, scanner, TV tuner card, digital camera, digital video camera, web camera, and the like. Further, in an exemplary, non-limiting embodiment, input device 936 can be POD 210. These and other input devices connect to the processing component 914 through the system bus 918 via interface port(s) 938. In a non-exhaustive listing, interface port(s) 938 can comprise any of a serial port, a parallel port, a game port, and a universal serial bus (USB). It is to be appreciated that output device(s) 940 can utilize some of the same type of ports as input device(s) 936. In an exemplary, non-limiting embodiment, a USB port may be used to provide input to computer 912, and to output information from computer 912 to an output device 940. An output adapter 942 can be utilized to facilitate communication with particular output devices 940 like monitors, speakers, and printers, among other output devices 940, which require special adapters. In a non-exhaustive listing, output adapters 942 can include video and sound cards provisioning a means of connection between the output device 940 and the system bus 918. It is to be appreciated that other devices and/or systems of devices also provide both input and output capabilities such as remote computer(s) 944. In a non-exhaustive listing, remote computer(s) 944 can be a personal computer, a server, a router, a network PC, a workstation, a microprocessor based appliance, a peer device or other common network node and the like, and can include, some or all of the components (both hardware and software) comprising computer 912. Information can be transmitted to remote computer(s) 944, where such information can comprise of 3D representation(s) 110, 240, plane data 120, 140, 160, 180, 195, 250, and image slice data 130, 150, 170, 190, 197, and 460, wherein the information can be stored in memory storage component 946. Further, remote computer(s) 944 can also provide any information to facilitate generation and orientation of an oblique plane in a 3D representation, wherein any necessary data, e.g., 3D representation data can be retrieved, or received, from memory storage component 946, for example where remote computer 944 is associated with an imaging system such as magnetic resonance imaging (MRI), computed tomography (CT), ultrasound, and the like employed to generate and capture imaging data.

Computer 912 can operate in a networked environment utilizing logical connections to one or more remote computers, such as remote computer(s) 944. Remote computer(s) 944 can be logically connected to computer 912 through a network interface 948 and further can be physically connected via communication component/connection 950. Network interface 948 encompasses communication networks such as local-area networks (LAN) and wide-area networks (WAN). In a non-exhaustive listing, LAN technologies include Fiber Distributed Data Interface (FDDI), Copper Distributed Data Interface (CDDI), Ethernet/IEEE 802.3, Token Ring/IEEE 802.5 and the like. In a non-exhaustive listing, WAN technologies include point-to-point links, circuit switching networks like Integrated Services Digital Networks (ISDN) and variations thereon, packet switching networks, and Digital Subscriber Lines (DSL).

Connection of the network interface 948 to the system bus 918 is facilitated by hardware/software comprising communication connection(s) 950. It is to be appreciated that while communication connection(s) 950 is shown located inside computer 912, communication connection(s) 950 can also be located externally to computer 912. In a non-exhaustive listing, hardware/software comprising communication connection(s) can comprise of internal and external technologies such as, modems including regular telephone grade modems, cable modems and DSL modems, ISDN adapters, and Ethernet cards. Where communications can be by any available means, e.g., in a non-exhaustive listing, wired, wireless, Wi-Fi, IEEE 802.11 (a,b,g,n), BLUETOOTH, RS-232 data, Wi-Fi Direct, WIMAX, Super WIFI, WLAN, radio, etc.

Exemplary Networked and Distributed Environments

One of ordinary skill in the art can appreciate that the various embodiments of systems and methods for controlling a plane in a 3D representation described herein can be implemented in connection with any computer or other client or server device, which can be deployed as part of a computer network or in a distributed computing environment, and can be connected to any kind of data store. In this regard, the various embodiments described herein can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Distributed computing provides sharing of computer resources and services by communicative exchange among computing devices and systems. These resources and services include the exchange of information, cache storage and disk storage for objects, such as files. These resources and services also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in video viewing and tagging mechanisms as described for various embodiments of the subject disclosure.

As mentioned above, while exemplary embodiments have been described in connection with various computing devices and network architectures, the underlying concepts may be applied to any network system and any computing device or system in which it is desirable to implement controlling orientation of a plane within a 3D representation to facilitate generation of image data associated with the plane.

Also, there are multiple ways to implement the same or similar functionality, e.g., an appropriate API, tool kit, driver code, operating system, control, standalone or downloadable software object, etc. which enables applications and services to take advantage of the techniques provided herein. Thus, embodiments herein are contemplated from the standpoint of an API (or other software object), as well as from a software or hardware object that implements one or more embodiments as described herein. Thus, various embodiments described herein can have aspects that are wholly in hardware, partly in hardware and partly in software, as well as in software.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used, for the avoidance of doubt, such terms are intended to be inclusive in a manner similar to the term "comprising" as an open transition word without precluding any additional or other elements when employed in a claim.

As mentioned, the various techniques described herein may be implemented in connection with hardware or software or, where appropriate, with a combination of both. As used herein, the terms "component", "module", "system", and the like, are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it can be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In view of the exemplary systems described supra, methodologies that may be implemented in accordance with the described subject matter can also be appreciated with reference to the flowcharts of the various figures. While for purposes of simplicity of explanation, the methodologies are shown and described as a series of blocks, it is to be understood and appreciated that the various embodiments are not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, some illustrated blocks are optional in implementing the methodologies described hereinafter.

In addition to the various embodiments described herein, it is to be understood that other similar embodiments can be used or modifications and additions can be made to the described embodiment(s) for performing the same or equivalent function of the corresponding embodiment(s) without deviating therefrom. Still further, multiple processing chips or multiple devices can share the performance of one or more functions described herein, and similarly, storage can be effected across a plurality of devices. Accordingly, the invention is not to be limited to any single embodiment, but rather is to be construed in breadth, spirit and scope in accordance with the appended claims.

What is claimed is:

1. A medical imaging system, comprising:
  a memory that stores computer-executable instructions; and
  a processor, communicatively coupled to the memory, that facilitates execution of the computer-executable instructions, further comprising:
  a three-dimensional (3D) representation; and
  a plane generation component configured to:
    receive, from a planar orientation device communicatively coupled to the plane generation component, a first positioning signal indicating a first orientation of the planar orientation device;
    establish a first orientation of a plane within the 3D representation, wherein the first plane of orientation is based at least in part on the first orientation of the planar orientation device;
    receive, from the planar orientation device, a second positioning signal indicating a second orientation of the planar orientation device; and
    establish a second orientation of the plane within the 3D representation, wherein the second plane of orientation is based at least in part on the second positioning signal received from the planar orientation device relative to a degree of motion of the planar orientation device from the first orientation of the planar orientation device, and during motion of the planar orientation device from receipt of the first positioning signal to receipt of the second positioning signal, temporarily disabling transmission of position signals from the planar orientation device to enable positioning of the planar orientation device without affecting the establishment of the second orientation of the plane relative to the first orientation of the plane.

2. The system of claim 1, further comprising a display device configured to render the 3D representation.

3. The system of claim 2, further comprising an image analysis component comprising instructions executable by the processor, wherein the image analysis component is configured to identify at least one of the first orientation of the plane and second orientation of the plane and, based thereon, incorporate information pertaining to the 3D representation creating at least one of a first imaged plane or a second imaged plane.

4. The system of claim 3, wherein the display device is further configured to display at least one of the first imaged plane or the second imaged plane with the 3D representation.

5. The system of claim 3, further comprising an image capture component configured to capture information associated with at least one of the first imaged plane or second imaged plane.

6. The system of claim 5, wherein the information is at least one of angular position, pixel data, medical information, or image information.

7. The system of claim 1, wherein the second orientation is established in response to a single motion of the plane generation component.

8. The system of claim 1, wherein the at least one positioning signal is generated by at least one of an accelerometer or a gyroscope comprising the planar orientation device.

9. The system of claim 1, wherein the 3D representation comprises data generated by at least one of a medical imaging system, magnetic resonance imaging, nuclear magnetic resonance imaging, magnetic resonance tomography, radiography, scintigraphy, 3D tomography, positron emission tomography, ultrasonography, or computed tomography.

10. The system of claim 1, wherein orientation of the planar orientation device from the first orientation to the second orientation is performed in free space.

11. The system of claim 1, wherein the planar orientation device is a hand-held device.

12. A method of medical imaging, comprising:
presenting a three-dimensional (3D) representation;
receiving, from a remotely located planar orientation device, a first positioning signal indicating a first orientation of the planar orientation device;
establishing, based at least in part on the first positioning signal, a first plane within the 3D representation;
receiving, from the planar orientation device, a second positioning signal indicating a second orientation of the planar orientation device relative to a degree of motion of the planar orientation device from the first orientation of the planar orientation device; and
determining, based on the second positioning signal, a second plane within the 3D representation, wherein during motion of the planar orientation device from the first orientation to the second orientation, temporarily disabling transmission of position signals from the planar orientation device to enable positioning of the planar orientation device without affecting determination of the position of the second plane relative to the first plane.

13. The method of claim 12, further comprising at least one of capturing information associated with at least one of the first plane or the second plane, or receiving positioning information pertaining to the first plane.

14. The method of claim 13, further comprising transmitting at least one of the captured first plane information or the captured second plane information.

15. The method of claim 12, further comprising presenting at least one of the first plane or the second plane with the 3D representation.

16. The method of claim 15, wherein at least one of the 3D representation, captured first plane information or the captured second plane information relate to data generated by at least one of a medical imaging system, magnetic resonance imaging, nuclear magnetic resonance imaging, magnetic resonance tomography, radiography, scintigraphy, 3D tomography, positron emission tomography, ultrasonography, or computed tomography.

17. A non-transitory computer readable storage medium comprising computer executable instructions that, in response to execution, cause a computing system including a processor to perform operations, comprising:
presenting a three-dimensional (3D) representation;
receiving, from a remotely located planar orientation device, a first positioning signal indicating a first orientation of the planar orientation device;
establishing, based at least in part on the first positioning signal, a first plane within the 3D representation;
receiving, from the planar orientation device, a second positioning signal indicating a second orientation of the planar orientation device relative to a degree of motion of the planar orientation device from the first orientation of the planar orientation device; and
determining, based on the second positioning signal, a second plane within the 3D representation, wherein during motion of the planar orientation device from the first orientation to the second orientation, temporarily disabling transmission of position signals from the planar orientation device to enable positioning of the planar orientation device without affecting determination of the position of the second plane relative to the first plane.

18. The non-transitory computer readable storage medium of claim 17, wherein the operations further comprise at least one of capturing information associated with at least one of the first plane or the second plane, or receiving positioning information pertaining to the first plane.

19. The non-transitory computer readable storage medium of claim 18, wherein the operations further comprise transmitting at least one of the captured first plane information or the captured second plane information.

20. The non-transitory computer readable storage medium of claim 17, wherein the operations further comprise presenting at least one of the first plane or the second plane with the 3D representation.

* * * * *